«12» United States Patent
Corradi et al.

(10) Patent No.: US 7,935,650 B2
(45) Date of Patent: May 3, 2011

(54) NEUTRALIZATION OF QUENCH STREAM IN A PROCESS FOR HANDLING CATALYST FROM AN OXYGENATE-TO-OLEFIN REACTION

(75) Inventors: Jason T. Corradi, Arlington Heights, IL (US); Lawrence W. Miller, Palatine, IL (US)

(73) Assignee: UOP LLC, Des Plaines, IL (US)

( * ) Notice: Subject to any disclaimer, the term of this patent is extended or adjusted under 35 U.S.C. 154(b) by 1002 days.

(21) Appl. No.: 11/612,424

(22) Filed: Dec. 18, 2006

(65) Prior Publication Data

US 2008/0146434 A1 Jun. 19, 2008

(51) Int. Cl.
*B01J 20/34* (2006.01)

(52) U.S. Cl. .......... 502/21; 585/638; 585/639; 585/640; 585/804; 585/809

(58) Field of Classification Search ................. 502/21; 585/638, 639, 640, 804, 809
See application file for complete search history.

(56) References Cited

U.S. PATENT DOCUMENTS

| 5,744,680 | A | 4/1998 | Mulvaney et al. | 585/640 |
|---|---|---|---|---|
| 6,121,503 | A | 9/2000 | Janssen et al. | 585/640 |
| 6,121,504 | A | 9/2000 | Kuechler et al. | 585/640 |
| 6,166,282 | A | 12/2000 | Miller | 585/638 |
| 6,187,983 | B1 | 2/2001 | Sun | 585/638 |
| 6,271,468 | B1 | 8/2001 | Layne | 174/50 |
| 6,293,999 | B1 | 9/2001 | Cheng et al. | 95/96 |
| 6,403,854 | B1 | 6/2002 | Miller et al. | 585/638 |
| 6,441,261 | B1 | 8/2002 | Kuechler et al. | 585/639 |
| 6,518,475 | B2 | 2/2003 | Fung et al. | 585/640 |
| 6,593,506 | B1 | 7/2003 | Searle | 585/639 |
| 6,593,906 | B2 | 7/2003 | Haba | 345/108 |
| 6,740,791 | B2 | 5/2004 | Kuechler et al. | 585/639 |
| 6,777,585 | B2 | 8/2004 | Van Egmond | 585/910 |
| 6,870,072 | B2 | 3/2005 | Lumgair et al. | 585/639 |
| 6,884,863 | B2 | 4/2005 | Van Egmond | 526/348 |
| 7,102,049 | B2 | 9/2006 | Ding et al. | 585/639 |
| 7,119,241 | B2 | 10/2006 | Beech et al. | 585/640 |
| 7,122,500 | B2 | 10/2006 | Chang et al. | 502/214 |
| 7,141,711 | B2 | 11/2006 | Van Egmond et al. | 585/640 |
| 2004/0064006 | A1 | 4/2004 | Beech et al. | 585/639 |

FOREIGN PATENT DOCUMENTS

| WO | WO 99/18055 | 5/1999 |
|---|---|---|
| WO | WO 01/60770 | 8/2001 |

OTHER PUBLICATIONS

Kirk-Othmer Encyclopedia of Chemical Technology, 4^{TH} Edition, vol. 9, John Wiley & Sons, 1996, pp. 249-271 and 894-899.

*Primary Examiner* — Prem C Singh
(74) *Attorney, Agent, or Firm* — Mark Goldberg

(57) ABSTRACT

The present invention provides a process for separating and disposing of catalyst in an oxygenate to olefins reaction system. Oxygenates are converted to olefins in a reactor in the presence of a catalyst having carbonaceous deposits, then effluent stream comprising the olefins is removed from the reactor. This effluent stream is entrained with a portion of the catalyst having carbonaceous deposits. The catalyst is separated from the effluent stream by contacting the effluent stream with a neutralized liquid quench medium to produce a catalyst containing stream. The carbonaceous deposits are incinerated and then the catalyst is recirculated to the reactor.

18 Claims, No Drawings

US 7,935,650 B2

NEUTRALIZATION OF QUENCH STREAM IN A PROCESS FOR HANDLING CATALYST FROM AN OXYGENATE-TO-OLEFIN REACTION

BACKGROUND OF THE INVENTION

The present invention relates to catalyst handling in a process for converting oxygenates to an olefin product. The present invention relates generally to a method of catalyst conservation in an oxygenate-to-olefin (OTO) process utilizing a fluidized oxygenate conversion zone and a relatively expensive catalyst and the use of a wet scrubbing step that recovers these contaminating catalyst particles in a scrubbing liquid which has organic bases or caustics added thereto to prevent a buildup of acid that adversely affects the catalyst.

The worldwide petrochemical industry is concerned with the production of light olefin materials such as ethylene and propylene for use in the production of numerous important chemical products. The main source for these materials is the steam cracking of petroleum feeds. The industry has long sought a source other than petroleum for the raw materials needed to supply the demand light olefin materials. The prior art has focused on different procedures for catalytically converting oxygenates such as methanol into the desired light olefin products. The major focus of routes to produce these desired light olefins has been on methanol conversion technology.

U.S. Pat. No. 6,403,854; U.S. Pat. No. 6,166,282 and U.S. Pat. No. 5,744,680 point to the use of a fluidized reaction zone along with a fluidized regeneration zone as the preferred commercial solution to the problem of effectively and efficiently using an ELAPO or SAPO-type of catalyst system in OTO service. The use of this technology gives rise to a substantial problem of solid-vapor separation to efficiently separate the particles of the fluidized catalyst from the vapor components exiting the OTO conversion zone. U.S. Pat. No. 6,166,282 shows a series of three cyclonic separation means to separate spent OTO catalyst from the product effluent stream. There still remains a very substantial problem of OTO or catalyst contamination of the product effluent stream withdrawn from the fluidized conversion zone.

U.S. Pat. No. 5,744,680 discloses the use of a wet scrubbing step on the cooled effluent stream from an OTO conversion zone to remove ELAPO molecular sieve-containing catalyst particles from this effluent stream but merely teaches the withdrawal of the catalyst-containing bottom stream from the wet scrubbing step for further unspecified treatment. U.S. Pat. No. 6,121,504 uses wet scrubbing to quench the effluent stream from the OTO conversion zone and produce a bottom stream which is recirculated to the wet scrubbing stream except for a drag stream that enters a stripping zone for purposes of heat recovery. U.S. Pat. No. 6,403,854 exemplifies a quench arrangement for the hot effluent stream recovered from the OTO conversion zone with first stage that removes catalyst fines entrained in the product effluent stream. U.S. Pat. No. 6,870,072 discloses the problem of product effluent contamination with catalyst particles and uses a wet scrubbing zone to remove these contaminating particles but no means of recovery and reuse of the catalyst particles. US 2004/0064006A1 discloses a process for efficient handling of catalyst fines. However, this published patent application does not recognize the problems that would be caused within that process with the buildup of acids that would adversely effect the catalyst.

A substantial economic problem for the OTO process is the amount of fresh catalyst that must be added to the OTO or fluidized conversion zone in order to maintain the catalyst inventory in the OTO conversion system when the product effluent stream contains substantial amounts of contaminating catalyst particles. This problem of effluent contamination by catalyst particles is because of the relatively high expense ELAPO or SAPO molecular sieves. This invention addresses the problem of reducing the loss of catalyst particles from a fluidized OTO conversion zone to decrease the consumption of relatively expensive catalyst thereby improving the economics of the OTO conversion process. The preferred oxygenate to olefin conversion process is generally referred to as a methanol-to-olefin(s), or MTO process, where methanol, is converted in a reactor to primarily ethylene and/or propylene in the presence of a catalyst—typically a molecular sieve catalyst made from a molecular sieve catalyst composition. This oxygenate to olefin reaction uses a catalyst that is maintained under operating conditions with carbonaceous deposits thereon. The carbonaceous deposits are often referred to as coke. Catalyst, for the purpose herein, is classified according to the size of the catalyst. Catalyst particles are larger than catalyst fines. Catalysts particles are typically retained in the reactor by the particle size separators that disengage or separate the catalyst particles from the effluent stream, which effluent stream passes through the particle size separators into the product recovery train. Catalyst fines are carried into the effluent stream.

Typically, catalyst particles above 40 microns in size are added to the reactor to catalyze a reaction. During the reaction, the catalyst develops carbonaceous deposits. Withdrawing a portion of the catalyst from the reactor and burning the carbonaceous deposits off of the catalyst particles controls the aggregate amount of the carbonaceous deposits on catalyst in the reactor. As the catalyst particles travel through the reactor, they break down into smaller particles due to contact between catalyst particles as well as with the various parts of the reactor. As they break down in size, they eventually become catalyst fines. Particle size separators, such as cyclones, are placed in the reactors and regenerators to retain useful catalyst particles in the reactor/regenerator system. Catalyst fines (typically less than 40 microns and more typically less than 20 microns) are generally not retained by the particle size separators and leave the regenerator through the flue. Catalyst fines in the reactor become carried into the effluent with the product.

The catalyst for an oxygenate to olefin reaction is typically a molecular sieve catalyst. It is formed into catalyst particles. The presence of the catalyst fines and large quantities of water make removal and disposal of both the water and catalyst fines a unique problem in the oxygenate to olefin process. The solution envisioned and provided by the present invention to this catalyst loss problem involves the use of a wet scrubbing step designed to recover substantially all of the product effluent contaminating catalyst particles and to provide a slurry of these catalyst particles in a scrubbing liquid such as water with subsequent recycle of at least a portion of the catalyst particles contained in the resulting slurry to the OTO conversion zone or to the associated deactivated OTO catalyst regeneration zone thereby recapturing the catalytic activity of these contaminating catalyst particles and diminishing the need for adding fresh catalyst to make-up for catalyst losses.

U.S. Pat. No. 6,403,854 describes a two-stage quench for use with the oxygenate conversion process. The first stage quench removes catalyst fines.

US 2004/0064006 A1 discloses a process for removal of catalyst fines using recycled quench streams. However, in the process taught therein, the recycled quench water will become more and more acidic over time, resulting either in damage to surfaces exposed to this recycled quench water or the need to utilize more expensive stainless steel metallurgy in any section of the equipment exposed to the acidic recycled quench water. Therefore, it would be desirable to have a process for the disposal and handling of catalyst fines that improves process efficiency while preventing the buildup of acids within the recycled quench water.

SUMMARY OF THE INVENTION

This invention provides a process for the disposal and handling of catalyst (including catalyst particles and catalyst fines, more specifically catalyst fines) that improves efficiency of their removal and disposal while preventing the buildup up of acids within the quench water used in the process.

The process of one embodiment comprises converting an oxygenate feedstock to an olefin product in a reactor using a catalyst (typically a molecular sieve catalyst) in the form of catalyst particles. The particles have carbonaceous deposits. Some of the catalyst particles break down into catalyst fines. The catalyst, typically in the form of catalyst fines, leaves the reactor in the effluent stream, which comprises an olefin product and water. Some of the catalyst particles that are in the effluent stream are in the range of about 20-40 microns in size that are desirable to recirculate for further use as catalyst. These particles would continue to function as catalyst and decrease the catalyst consumption. True catalyst fines that are at least less than 20 microns and preferably less than 10 microns in size would be removed by catalyst recovery devices, either for further use as catalyst or at a minimum they would pass through the regenerator and exit through the flue gas. A cleaner waste product would be produced after the coke is burned off in the regenerator.

The catalyst in the effluent is separated from the olefin product by contacting the catalyst with a liquid quench medium. The contact of the liquid quench medium removes the catalyst from the effluent stream, including the olefin product; this contact forms a catalyst containing stream. Finally, the carbonaceous deposits on the catalyst from the catalyst containing stream are incinerated to remove at least a portion of the carbonaceous deposits from the catalyst. The effluent stream withdrawn from the reactor comprises from about 30 wt-% to about 70 wt-% water. This quenching step may be done in a solids wash device, such as a quench device or a quench tower, including but not limited to a hydrocyclone, such as a venturi quench. The catalyst is concentrated in the water to produce a concentrated catalyst stream from which the catalyst that is of sufficient size to continue use as catalyst is removed and returned to the reactor. It has been found efficient to recycle the quench water. However, the quench water will experience an increase in organic acids if precautions are not taken to maintain the pH of the quench water. Computer simulations indicate that the pH of the quench water will be about 4 which is an acidity level requiring more expensive stainless steel metallurgy within any section of the plant that would be in contact with acidic quench water.

In one embodiment of the invention, organic bases, such as amines, are used to neutralize acetic acid that will condense and accumulate in the pumparound liquid from a single-stage quench tower. An advantage to the use of the amines is that a separate stage in the quench tower for neutralization is not necessary (as it is with the use of caustics). A single-stage quench tower design is sufficient.

In another embodiment of the invention, caustics such as NaOH is used to neutralize the acids that build up in the quench tower. A design that has been found useful for this purpose involves a quench tower that is divided into three sections or stages. In the bottom stage, the product effluent is completely desuperheated by direct contact with a water pumparound over disc and donut style trays. Product water from the product separator is added to the bottom pumparound to replenish the water vaporized during quenching. The bottom pumparound scrubs solids, such as catalyst fines, from the reactor effluent vapor. The effluent vapor will contain acetic acid, which will condense and accumulate in the pumparound. Heavy feed contaminants are directed to the bottom pumparound via the feed stripper bottoms purge. Heavy reaction by-products will also condense into the pumparound. These heavy contaminants along with catalyst fines are removed via the waste water drag stream.

The scrubbed vapor effluent from the bottom stage of the quench tower rises into the middle stage. In the middle stage, the vapor is contacted with a mild (<such as mild NaOH) caustic solution to neutralize and remove organic acids. This contact may involve conventional contacting devices such as disk and donut trays or other types of trays or packing. The trays would need to be of the weir-less type, so that fines did not build up and clog them. Since the caustic will poison the catalyst fines, neutralization occurs in this separate stage after the catalyst fines have been scrubbed out. Dissolved solids in the middle pumparound are controlled by using a drag stream to spent caustic disposal.

The top stage of the quench tower provides a washing of the reactor effluent vapor. The scrubbed and neutralized vapor is contacted with a water pumparound across conventional trays to wash out any entrained caustic from the middle stage. Stripped water is added as a clean make-up to the upper pumparound to maintain liquid levels in the top stage.

In yet another embodiment of the present invention, A two-stage quench tower design is proposed to recover catalyst fines prior to neutralization. The reactor effluent is quenched and the catalyst fines are removed in the lower stage of the tower. Neutralization of organic acids occurs in the upper stage of the tower. A drag stream from the quench tower bottoms pumparound is sent to a solids removal system. The solids-depleted stream is then sent to the upper pumparound to dilute the circulating caustic. Waste water is removed from the upper section of the tower.

DETAILED DESCRIPTION OF THE INVENTION

This invention provides a process that provides for the neutralization of the quench medium that is used to remove catalyst fines. This neutralization prevents a build up of organic acids from adversely affecting the catalyst and the overall process of conversion of oxygenates to olefins. In one embodiment of the invention, organic bases, such as amines, are used to neutralize acetic acid that will condense and accumulate in the pumparound liquid from a single-stage quench tower. An advantage to the use of the amines is that a separate stage in the quench tower for neutralization is not necessary (as it is with the use of caustics). A single-stage quench tower design is sufficient in this embodiment of the invention.

In another embodiment of the invention, caustics such as NaOH are used to neutralize the acids that build up in the quench tower. A design that has been found useful for this purpose involves a quench tower that is divided into three sections or stages. In the bottom stage, the product effluent is completely desuperheated by direct contact with a water pumparound over disc and donut style trays. Product water from the product separator is added to the bottom pumparound to replenish the water vaporized during quenching. The bottom pumparound scrubs solids, such as catalyst fines, from the reactor effluent vapor. The effluent vapor will contain acetic acid, which will condense and accumulate in the pumparound. Heavy feed contaminants are directed to the bottom pumparound via the feed stripper bottoms purge. Heavy reaction by-products will also condense into the pumparound. These heavy contaminants along with catalyst fines are removed via the waste water drag stream.

The scrubbed vapor effluent from the bottom stage of the quench tower rises into the middle stage. In the middle stage, the vapor is contacted with a mild (<1 wt-% NaOH) caustic solution across conventional trays to neutralize and remove organic acids. Since the caustic will poison the catalyst fines, neutralization occurs in this separate stage after the catalyst fines have been scrubbed out. Dissolved solids in the middle pumparound are controlled by using a drag stream to spent caustic disposal. The pH in the middle pumparound is maintained by diluting the pumparound with water from the upper pumparound.

The top stage of the quench tower provides a washing of the reactor effluent vapor. The scrubbed and neutralized vapor is contacted with a water pumparound across conventional trays to wash out any entrained caustic from the middle stage. Stripped water is added as a clean make-up to the upper pumparound to maintain liquid levels in the top stage.

The process for making the olefins comprises converting an oxygenate feedstock to an olefin product in a reactor uses catalyst particles that have carbonaceous deposits in the particles. The catalyst particles break down into catalyst fines. The catalyst fines leave the reactor and become entrained in the effluent stream. The effluent stream is mostly made of olefin product and water. The catalyst fines are then separated from the effluent stream. The catalyst fines are separated from the olefin product by condensing at least a portion of the water or alternatively, contacting the effluent stream with a quench medium that is at about a neutral pH. Depending upon the configuration, organic bases or caustics are added to the quench medium to avoid a harmful acidic environment. The quench medium or condensed water contacts the catalyst fines. The contacting removes the catalyst fines from the remainder of the effluent stream, and in particular the olefin product; this contacting forms a catalyst containing stream. Finally, if too small to regenerate and return to the reactor, the catalyst fines are incinerated to remove at least a portion of the carbonaceous deposits from the catalyst fines.

The feedstock used in the present invention contains one or more oxygenates. In the most preferred embodiment, the feedstock is selected from one or more of methanol, ethanol, dimethyl ether, diethyl ether or a combination thereof, more preferably methanol and dimethyl ether, and most preferably methanol. The feedstock is preferably converted into ethylene and/or propylene. The most preferred process is generally referred to as a methanol-to-olefins (MTO) process. In a MTO process, typically an oxygenated feedstock, most preferably a methanol containing feedstock, is converted in the presence of a methanol to olefins catalyst or catalyst composition. In one embodiment, the catalyst or catalyst composition is a molecular sieve catalyst composition that converts the feedstock into one or more olefin(s), preferably and predominantly, ethylene and/or propylene, often referred to as light olefin(s)

The preferred molecular sieves include aluminophosphate (ALPO) molecular sieves and silicoaluminophosphate (SAPO) molecular sieves and substituted, preferably metal substituted, ALPO and SAPO molecular sieves including the molecular sieves that are intergrowth materials having two or more distinct phases of crystalline structures within one molecular sieve composition. The most preferred molecular sieve is SAPO-34. Other molecular sieves as known to those skilled in the art may be employed.

The feedstock often contains one or more diluent(s), typically used to reduce the concentration of the feed stock, and are generally non-reactive to the feedstock or molecular sieve catalyst composition. Water is frequently used as the diluent.

The reaction processes can take place in a variety of catalytic reactors such as hybrid reactors that have a dense bed or fixed bed zones and/or fast fluidized bed reaction zones coupled together, circulating fluidized bed reactors, riser reactors, and the like. In the preferred embodiment, a fluidized bed process or high velocity fluidized bed process includes a reactor system, a regeneration system and a recovery system. The reactor system preferably is a fluid bed reactor system having a first reaction zone within one or more riser reactor(s) and a second reaction zone within at least one disengaging vessel, preferably comprising one or more cyclones. The feedstock entering the reactor system is preferably converted, partially or fully, in the first reactor zone into an effluent stream that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the effluent stream containing one or more olefin(s) within the disengaging zone. Cyclones are particle size separators and retain catalyst above a threshold size. Catalyst below a threshold size passes through the cyclones in the effluent stream. As defined above, catalyst particles are retained by the cyclones in the reactor. Catalyst fines pass through the cyclones into the effluent stream The coked molecular sieve catalyst composition is withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, under general regeneration conditions of temperature, pressure and residence time.

The effluent stream is withdrawn from the reactor and is passed through a solids wash, and in one embodiment a quench, to cool the effluent stream, remove a majority of the water in the effluent stream and remove solids such as catalyst fines. Alternatively, one or more heat exchangers are used to remove the heat of the effluent stream before quenching the effluent stream. The solids wash, by removing the catalyst fines, prevents the recovery train downstream from the quench from being fouled with catalyst fines.

The regenerator as used herein includes not only the regenerator apparatus itself, but also the regenerator flue, which is a conduit or pipe that carries the incinerated gasses and incinerated catalyst fines from the regenerator.

A solids wash (or solids wash device) is defined, for purposes herein, as a device that is downstream from the reactor that removes solid particles such as catalyst including catalyst particles and catalyst fines from the effluent stream. The solids wash device is configured to contact solid phase particles suspended in the gas phase of an effluent stream with a sufficient quantity of liquid and mechanical energy to remove solid particles from the gas phase into the liquid.

The solids wash device is a quench tower or a hydrocyclonic separator such as a venturi quench (hereinafter individually referred to as a "quench device" or "quench". As noted, the effluent stream from an oxygenate to olefin reactor is quenched directly by contacting a suitable quench medium in a quench tower. A portion of the effluent stream is gaseous under quenching conditions. The gaseous stream comprises light olefins, dimethyl ether, methane, CO, $CO_2$, ethane, propane, and any water and unreacted oxygenate feedstock that is not condensed during the operation of the solids wash device. The compounds in the effluent stream, that are liquid under quenching conditions, are separated from the gaseous effluent stream as a fines stream (or quench bottoms stream). The quench bottoms stream comprises catalyst fines and quench medium, typically water, and a portion of the water quenched from the effluent stream. The quench bottoms stream also comprises a portion of the unreacted oxygenate feedstock) and a small portion of the oxygenate conversion by-products, particularly heavy hydrocarbons ($C_5^+$) and oxygenate byproducts.

Preferably, a quench medium is selected from a composition which remains substantially as a liquid under the quenching conditions, thus minimizing the amount of the quench medium present in the light gaseous product fraction which must undergo more expensive gaseous product processing steps to recover commercially acceptable grades of light olefin products. More preferably, the quench medium is a stream that is substantially water and is selected from the several fractions of the bottoms stream from the solids wash device or "quench bottoms stream."

In particular, the quench bottoms stream is separated into a fraction that is used as a quench medium ("quench recycle fraction"). The quantity of this quench recycle fraction depends on the overall amount of heat that needs to be removed from the effluent stream in the operation of the solids wash device, and the temperature of the quench medium introduced into the solids wash device.

According to one embodiment, it is desirable to condense substantially all of the water in the effluent stream. According to this embodiment, the weight ratio of quench medium to effluent stream ranges from about 3.5:1 to about 5.5:1; preferably from about 4.0:1 to about 5.0:1; more preferably from about 4.2:1 to about 4.7:1. The temperature of the quench medium entering the solids wash device is less than 90° C.; preferably from about 20° to about 70° C.; more preferably from about 20° to about 45° C.; most preferably about 35° C.

Optionally, the quench bottoms stream is pressurized and used for providing heat to other streams. In one embodiment, the quench bottoms stream (or any, or all of the several fractions into which the quench bottoms stream is divided, or streams from quench medium separations thereof) is used directly as a heat exchanger fluid to increase the heat content and/or temperature of the oxygenate feedstock at one or more of the stages with successively higher heat contents. Further, any of the several fractions or streams produced from the quench medium separations thereof can be used as a heat source of other streams within the overall oxygenate conversion reaction and product recovery process. For example, the quench bottoms stream is used in a heat exchanger to heat the reboiler at the bottoms of a deethanizer, demethanizer, depropanizer or a $C_3$ splitter (propane-propylene splitter). Once a quench bottoms stream, or one or more fractions or streams produced from the quench medium separations is used a heat source in other parts of the process, it is cooled by such use. The cooled quench bottoms recovered from such uses is optionally returned back to the solids wash device and can be used as a quench medium.

One solids wash device of one embodiment is a hydrocyclone. Cyclone separators of the type that are used for solids washes create a vortex motion that causes the heavier particles and liquids to be concentrated on the radial outward surface of the vortex and the lighter gases radially inward. The cyclone separator has a quench medium that is sprayed into its top end. The effluent stream enters the cyclone separator at a tangential inlet. The quench medium contacts the effluent stream, cools and condenses at least a portion of the effluent stream. The liquid also contacts the solids, including catalyst fines, in the effluent stream. The liquid contacting creates larger, less buoyant, water saturated particles that are forced radially outward by the vortex away from the less dense, gaseous portion of the effluent stream. One type of cyclone separator is a venturi quench. Venturi quenches are known in the art and are found in Perry's CHEMICAL ENGINEERS HANDBOOK, 6th Edition, section 20, pages 93 et. seq. (1984). Cyclone separators are designed to remove all or substantially all of the solids, including catalyst fines, with relatively small amounts of water.

The solids wash device, including a quench device, cyclone separator, pre-quench or venturi quench produces a quench bottoms stream that comprises water and catalyst fines. The quench bottoms stream comprising water and catalyst fines can be directed to an incinerator to be incinerated. Alternatively, the catalyst fines from the bottoms stream of the solids wash device, or dilute fines stream, are concentrated to produce a concentrated fines stream before being sent to an incinerator (e.g., a regenerator). The concentration is done with a clarification unit, filtration unit, or a centrifugal separator. Other methods known in the art for separating particulate from water also can be used.

Due to the small particle size of the catalyst fines, the particles produce a stable, fluid slurry readily transported, injected and distributed into the regenerator. According to one embodiment, the catalyst fines are less than 40 microns; preferably less than 20 microns; more preferably less than 10 microns.

The cooling effect of the evaporation of the water in the slurry can be offset by the heat of combustion of the carbonaceous deposits in the catalyst fines. In another embodiment, dilute streams are added to the regenerator. Certain streams containing catalyst require more heat to evaporate the water in the dilute stream than is produced by the burning of catalyst fines. Use of such streams can reduce the load on the catalyst cooler (i.e., the device that cools the catalyst in the regenerator or leaving the regenerator.

The catalyst particles can be entrained in the effluent stream. Entrainment of catalyst particles can occur when a particle size separator malfunctions or loses efficiency due to wear and tear. Without recovery of these catalyst particles, valuable catalyst inventory can be lost. Recovery of catalyst particles is possible when the catalyst particles are washed from the effluent stream in a solids wash and then are transported to the regenerator. Unlike the smaller catalyst fines which are removed and disposed of, the recovered catalyst particles will remain in the reactor/regenerator catalyst cycle. The catalyst can then return to functioning provided that catalyst was not damaged in the process of recovering and returning the catalyst particles the regenerator.

One solids wash system has a first and second phase. The first phase is a pre-quench, which partially condenses the water to remove the catalyst fines from the effluent stream in a concentrated portion. The second phase is a separate product separator that further condenses the water in the effluent stream to remove substantially all of the remaining water in the effluent stream. The bottoms stream of the first phase quench or pre-quench comprises a relatively concentrated amount of catalyst fines compared to a quench device that is operated to remove all of the water in the effluent stream in one stage. In one embodiment, a majority of the catalyst fines that leave the reactor are in the pre-quench bottoms stream. By majority, it is meant to be substantially more than 50%.

In one aspect of a two-stage quench embodiment of the invention, the first phase quench produces an overhead stream and quench bottoms stream. The quench bottoms stream has a concentration of catalyst fines ranging from about 0.1 wt-% to about 10 wt-%; preferably from about 0.1 wt-% to about 5 wt-%; more preferably from about 0.15 wt-% to about 4 wt-% based on total weight of the quench bottoms stream.

After the first phase quench, the amount of water in the overhead stream of the first phase quench device ranges from about 1 wt-% to about 60 wt-%; preferably from about 20 wt-% to about 55 wt-%; more preferably from about 30 wt-% to about 50 wt-% based upon the total weight of the overhead stream. The remaining effluent stream from the overhead stream of the first phase quench is directed to the inlet of the second phase quench device as described below.

The second phase is for dewatering the effluent stream. The second phase quench device quenches substantially all of the remaining water in the effluent stream. Since, most of the solids have been previously removed and the effluent stream is substantially free of solids, the bottoms stream of the second phase quench device has very little catalyst fines in the water of the bottoms stream.

The overhead of the second phase quench device is an olefin stream that has little more water than the saturation level of the remaining dewatered effluent stream. According to one embodiment, the amount of water in the effluent stream after the second phase is less than about 5 wt-%; more preferably less than about 3 wt-% of the total water in the effluent stream leaving the reactor.

According to one embodiment, the catalyst fines have been removed from the effluent stream after the second phase quench. Following, the second phase quench, the effluent is directed to a compression train, caustic wash, dryers and the recovery train as described below.

Now that water and catalyst (e.g. catalyst particles and catalyst fines, more particularly catalyst fines) is removed other steps are taken to recover product. There are many well known recovery systems, techniques and sequences that are useful in separating olefin(s) and purifying olefin(s) from the effluent stream. Recovery systems generally comprise one or more or a combination of a various separation, fractionation and/or distillation towers, columns, splitters, or trains, reaction systems and other associated equipment for example various condensers, heat exchangers, refrigeration systems or chill trains, compressors, knock-out drums or pots, pumps, and the like.

Non-limiting examples of equipment used in a recovery system include one or more of a demethanizer, preferably a high temperature demethanizer, a deethanizer, a depropanizer, a wash tower often referred to as a caustic wash tower, absorbers, adsorbers, membranes, ethylene ($C_2$) splitter, propylene ($C_3$) splitter, butene ($C_4$) splitter, and the like.

Generally accompanying most recovery systems is the production, generation or accumulation of additional products, by-products and/or contaminants along with the preferred prime products. The preferred products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Non-limiting examples of contaminants and by-products include generally polar compounds such as water, alcohols, carboxylic acids, ethers, carbon oxides, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example for the purification of olefin(s), are described in Kirk-Othmer ENCYCLOPEDIA OF CHEMICAL TECHNOLOGY, 4th Edition, Volume 9, John Wiley & Sons, 1996, pages 249-271 and 894-899, which is herein incorporated by reference. Purification systems are also described in, for example, U.S. Pat. No. 6,271,428 (purification of a diolefin hydrocarbon stream), U.S. Pat. No. 6,293,999 (separating propylene from propane), and U.S. Pat. No. 6,593,506 (purge stream using hydrating catalyst), which is herein incorporated by reference.

Typically, in converting one or more oxygenates to olefin (s) having 2 or 3 carbon atoms, an amount of hydrocarbons, particularly olefin(s), especially olefin(s) having 4 or more carbon atoms, and other by-products are formed or produced. Included in the recovery systems of the invention are reaction systems for converting the products contained within the effluent stream withdrawn from the reactor or converting those products produced as a result of the recovery system utilized.

The effluent stream removed from a conversion process, particularly a MTO process, typically has a minor amount of hydrocarbons having 4 or more carbon atoms. The amount of hydrocarbons having 4 or more carbon atoms is typically in an amount less than 30 wt-%, preferably less than 25 wt-%, more preferably less than 20 wt-%, and most preferably less than 15 wt-%, based on the total weight of the effluent stream withdrawn from a MTO process, excluding water. In particular with a conversion process of oxygenates into olefin(s) utilizing a molecular sieve catalyst composition the resulting effluent stream typically comprises a majority of ethylene and/or propylene and a minor amount of four carbon and higher carbon number products and other by-products, excluding water.

The preferred light olefin(s) produced by any one of the processes described above, preferably conversion processes, are high purity prime olefin(s) products that contains a $C_X$ olefin, wherein x is a number from 2 to 4, in an amount greater than 80 wt-%, preferably greater than 90 wt-%, more preferably greater than 95 wt-%, and most preferably no less than about 99 wt-%, based on the total weight of the olefin.

Other conversion processes, in particular, a conversion process of an oxygenate to one or more olefin(s) in the presence of a molecular sieve catalyst composition, especially where the molecular sieve is synthesized from a silicon-, phosphorous-, and alumina-source, include those described in for example: U.S. Pat. No. 6,121,503 (making plastic with an olefin product having a paraffin to olefin weight ratio less than or equal to 0.05), U.S. Pat. No. 6,187,983 (electromagnetic energy to reaction system), WO 99/18055 published Apr. 15, 1999 (heavy hydrocarbon in effluent stream fed to another reactor) WO 01/60770 published Aug. 23, 2001 and U.S. Pat. No. 6,441,261 (high pressure), and U.S. Pat. No. 6,518,475 (acetone co-fed), which are all herein fully incorporated by reference.

This oxygenate containing stream, or crude methanol, typically contains the alcohol product and various other components such as ethers, particularly dimethyl ether, ketones, aldehydes, dissolved gases such as hydrogen methane, carbon oxide and nitrogen, and fusel oil. The oxygenate containing stream, crude methanol, in the preferred embodiment is passed through a well known purification processes, distillation, separation and fractionation, resulting in a purified oxygenate containing stream.

The oxygenate containing stream or purified oxygenate containing stream, optionally with one or more diluents, is contacted with one or more molecular sieve catalyst composition described above in any one of the processes described above to produce a variety of products, particularly light olefin(s), ethylene and/or propylene.

In a more fully integrated process, olefin(s) produced are directed to, in one embodiment, one or more polymerization processes for producing various polyolefins. In addition to polyolefins, numerous other olefin derived products are formed from the olefin(s) recovered any one of the processes described above, particularly the conversion processes, more particularly the GTO process or MTO process. These include, but are not limited to, aldehydes, alcohols, acetic acid, linear alpha olefins, vinyl acetate, ethylene dichloride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes.

The foregoing description of the invention is intended to illustrate one or more embodiments of the invention and is non-limiting. While the invention has been described herein in terms of the advantages, features, and applications disclosed, it will be apparent to a person of ordinary skill in the art that the invention can be used in other instances. Other modifications and improvements can be made without departing from the scope of the invention.

What is claimed is:

1. A process for separating and reusing of catalyst in an oxygenate to olefins reaction system, the process comprising the steps of:
   (a) converting oxygenates to olefins in a reactor in the presence of a catalyst having carbonaceous deposits;
   (b) withdrawing from the reactor an effluent stream comprising the olefins, the effluent stream being entrained with a portion of the catalyst having carbonaceous deposits;
   (c) contacting the effluent stream with a neutralized quench medium in a quench tower to produce a catalyst-containing stream separated from said effluent stream;
   (d) neutralizing the quench medium in a separate stage of the quench tower;
   (e) incinerating in an incinerator the carbonaceous deposits that are in the portion of the catalyst in the catalyst-containing stream; and
   (f) sending the incinerated catalyst-containing stream to the said reactor.

2. The process of claim 1 wherein the reactor is selected from the group consisting of moving bed and riser reactors.

3. The process of claim 1 wherein the catalyst is a molecular sieve catalyst.

4. The process of claim 1 wherein said neutralized liquid quench medium contains at least one nitrogen containing organic base.

5. The process of claim 1 wherein said neutralized liquid quench medium contains at least one caustic metallic base.

6. The process of claim 4 wherein said nitrogen containing organic base decomposes within said quench tower.

7. The process of claim 1 wherein said quench tower comprises:
   a) a bottom stage wherein a product effluent is desuperheated by direct contact with water and wherein said water scrubs solids from said product effluent;
   b) a middle stage into which rises effluent vapor from said bottom stage and wherein said effluent vapor is contacted with a mild caustic solution to neutralize and remove organic acids from said effluent vapor and wherein dissolved solids are controlled by use of a drag stream; and
   c) a top stage wherein said reactor effluent vapor is further washed by water to remove any remaining caustics from said reactor effluent.

8. The process of claim 7 wherein water from a product separator is added to said water in said bottom first stage.

9. The process of claim 7 wherein said solids scrubbed from said bottom stage are separated in a catalyst fines separation stage.

10. The process of claim 7 wherein said mild caustic solution comprises a mild sodium hydroxide solution.

11. The process of claim 7 wherein water is added to said middle stage from within said top stage.

12. The process of claim 1 wherein said quench medium contacts said effluent stream in a quench tower containing at least two stages wherein said at least two stages comprise a lower stage and an upper stage.

13. The process of claim 12 wherein said catalyst fines are removed from said effluent stream in said lower stage.

14. The process of claim 12 wherein said reactor effluent is neutralized in said upper stage by a dilute caustic pumparound stream.

15. The process of claim 14 wherein said upper stage contains trays for contact between said reactor effluent and said dilute caustic pumparound stream.

16. The process of claim 12 wherein a drag stream from said lower stage removes said catalyst fines to a solids removal system.

17. The process of claim 12 wherein a portion of water in said drag stream is removed and returned to said upper stage.

18. The process of claim 12 wherein said caustic base is sodium hydroxide.

* * * * *